United States Patent [19]
Becker

[11] Patent Number: 6,113,567
[45] Date of Patent: Sep. 5, 2000

[54] LACRIMAL SILICONE TUBE WITH REDUCED FRICTION

[76] Inventor: Bruce B. Becker, 24371 Rolling View Rd., Hidden Hills, Calif. 91302

[21] Appl. No.: 09/133,986

[22] Filed: Aug. 13, 1998

Related U.S. Application Data

[63] Continuation of application No. 08/547,792, Oct. 25, 1995, abandoned.

[51] Int. Cl.[7] .................................................... A61M 5/00
[52] U.S. Cl. .............................. 604/8; 604/264; 604/265; 427/489; 427/491
[58] Field of Search ...................................... 604/8–10, 28, 604/500, 264, 265, 523, 285, 289, 290, 294, 175, 101; 128/898; 623/11, 12, 66; 401/49; 427/2.1, 2.12, 2.24, 2.25, 2.28, 2.3, 574, 578, 579, 583, 489, 491

[56] References Cited

U.S. PATENT DOCUMENTS

| | | | |
|---|---|---|---|
| 3,962,519 | 6/1976 | Rüsch et al. | |
| 4,335,723 | 6/1982 | Patel | |
| 4,693,704 | 9/1987 | Ogita | 604/101 |
| 4,751,924 | 6/1988 | Hammerschmidt et al. | 604/101 |
| 4,932,958 | 6/1990 | Reddy et al. | 606/192 |
| 4,990,139 | 2/1991 | Jang | 604/101 |
| 5,135,474 | 8/1992 | Swan et al. | 604/8 |
| 5,415,636 | 5/1995 | Forman | 604/101 |

Primary Examiner—Corrine McDermott
Attorney, Agent, or Firm—Trexler, Bushnell, Giangiorgi & Blackstone, Ltd.

[57] ABSTRACT

Lacrimal tissue inflammation and scarring is minimized when an ostium formed by balloon dacryocystorhinostomy is stented by a silicone member having a stent portion which may be treated to reduce friction between the stent portion and tissue supporting the lacrimal mucosal surface when the silicone member moves due to blinking. The stent portion may be treated by plasma deposition of a vaporized silicone based monomer upon the outer surface of the silicone member which is covalently bonded to the silicone member thereby forming a silicone polymer coating which is very smooth and pit-free. The member has a thin central segment of relatively small outer diameter, a pair of fat segments of relatively large outer diameter at opposite ends thereof, and thin end segments connected to the fat segments. The stent portion is formed from the central segment and the proximate end portions of the fat segments. The member is inserted in the lacrimal system, by threading each end segment from the eye through a respective punctum, a canaliculus, the lacrimal sac and the ostium into the nasal cavity. The member is pulled down the nasal cavity by grasping the thin end segments while pulling the fat segments in the opposite direction less forcefully to stretch and thereby reduce the thickness of the fat segments so that they more easily move through the lacrimal system. After the stent portion is brought into place, the untreated portions of the member are severed.

19 Claims, 3 Drawing Sheets

LACRIMAL SILICONE TUBE WITH REDUCED FRICTION

This application is a continuing application of Ser. No. 08/547,792, filed on Oct. 25, 1995, now abandoned.

BACKGROUND OF THE INVENTION

1. Field of the Invention

This invention relates to lacrimal silicone tubes and a method of inserting the same, and more particularly, to lacrimal silicone tubes which are treated to reduce the friction between the tube and the supporting tissue.

2. Description of the Prior Art

Tears bathe the surface of the eye and then drain into puncta and canaliculi on the medial upper and lower lids. The tears flow from the canaliculi into the lacrimal sac down the nasolacrimal duct into the nose.

The nasolacrimal duct can become obstructed either congenitally or by an acquired obstruction in adulthood. When the nasolacrimal duct becomes obstructed, tears can no longer drain from the surface of the eye through the lacrimal system into the nose. The tears therefore well up over the eyes and spill over the lids onto the face and the patient has to constantly dab the eyes with a tissue. In addition, tears stagnate in the lacrimal sac which allows bacteria to multiply. The lacrimal sac then becomes infected (dacryocystitis). Dacryocystitis causes the lacrimal sac to become swollen, red, and painful. Pus exudes from the lacrimal sac through the canaliculi onto the eye and results in purulent material constantly covering the eye. In time, the dacryocystitis does not respond to antibiotics and surgery becomes necessary.

Dacryocystorhinostomy (DCR) is the surgery used to correct nasolacrimal duct obstruction. In a DCR a new opening (ostium) is created between the lacrimal sac and the nose. This allows tears to flow from the lacrimal sac through the DCR ostium into the nose. An open or incisional DCR requires an incision on the side of the nose. In an open DCR, a large DCR ostium is created by making a 17 mm. plus opening in mucosa and bone. This procedure has significant morbidity, a prolonged recovery, and the threat of scarring and hemorrhage. In contrast, a balloon DCR has much less morbidity, no incision, and a quick recovery. The balloon DCR ostium is smaller (5 mm.) Than that of an open DCR. Because the balloon DCR ostium is only 5 mm. in diameter, a stent is required to keep the DCR ostium open after surgery. Otherwise, postoperative inflammation and scarring may cause it to close.

A silicone tube is typically used to stent the ostium. The tube has metal probes at each end and may be inserted by pulling one probe and tube end through a punctum, a canaliculus, the lacrimal sac, and the ostium into the nasal cavity. The opposite end of the tube and its attached probe is then brought through the opposing punctum and canaliculus, the lacrimal sac, and the ostium into the nasal cavity. The probes are then grasped in the nasal cavity and brought down the nose and out the external naris, pulling the tube into position to stent the ostium, puncta, canaliculi and lacrimal sac. The tube is left in place as a stent for six months.

It has been found, however, that silicone tube stents induce lacrimal tissue reaction and inflammation. The inflammation lead, in time, to increased scar contraction around the ostium. Although this problem has existed for many years, no one has discovered the cause of this tissue reaction and inflammation, and no effective solutions have been suggested by the prior art.

Various balloon dilation catheters and methods using them are shown in U.S. Pat. No. 5,169,386. As stated at col. 3, lines 47–51, and col. 9, line 61, col. 10, line 2, it is desirable for the catheter to include a lubricous coating to facilitate insertion of the catheter into the lacrimal system. The coating may be a silicone coating bonded to the catheter or may be a topical coating of silicone oil. It is also suggested at col. 13, lines 62–65, that the necks of the balloon be plasma etched. The patent discusses prior art use of a silicone tube stent in an attempt to maintain patency of the ostium (col. 1, lines 61–64) and prior art use of a balloon catheter as a stent with the inflated balloon used to retain the stent in place (col. 2, lines 4–13).

The prior art teaches that stents used for other purposes can be coated. Medi-tech Boston Scientific Corporation sells ureteral stents which are coated with "Glidex" coating. This coating is said to produce a hydrophilic surface at least eight times more slippery than an uncoated surface for reducing buckling during advancement, for facilitating crossing of tight strictures and for easing negotiation of difficult curves and advancement through stone-obstructed tracts.

Kurihashi, *Opthalmologica,* 1993 No. 206, pp. 57–68, teaches recanalization of the lacrimal passage with silicone tubing which consists of three pieces: a thinner central segment joined to two thicker outer segments with sealed distal ends. The tubing extends through the upper and lower canaliculi and the nasolacrimal duct.

SUMMARY OF THE INVENTION

According to the invention, it has been discovered that the lacrimal tissue reaction and inflammation is caused by movement of the silicone stent and the friction between the stent and the supporting lacrimal tissue. Microscopic examination of the surface of the silicone tube reveals that it is pitted, and it is believed that this pitted surface contributes to the friction when there is relative movement between the stent and the lacrimal tissue. This relative movement is caused by blinking. When the eyelid closes during blinking, the silicone tube is forced further into the nose. When the lid opens, the tube is pulled back to its original position in the lacrimal system. With each blink, the tube moves back and forth across the lacrimal mucosal surface, generating friction and increasing tissue inflammation. During the six months the tube is left in place, the patient blinks tens of thousands of times. The friction between the tube and the lacrimal mucosa is therefore a major factor in lacrimal tissue reaction and inflammation.

It is a principle of the invention that this friction can be reduced by treating the surface of the stent to reduce friction. In particular, the friction is reduced by coating the surface with a plasma polymerizate of silicone. The coating is applied in a process in which a vaporized silicone monomer in a glow zone is deposited and covalently bonded to the silicone tube forming a silicone polymer surface.

This surface is much smoother than the surface of an untreated silicone tube and is substantially pit-free. As a result, lacrimal tissue reaction, inflammation and scarring are reduced. The ostium is larger after stent removal, and closure of the ostium is less likely. Corticosteroids are normally used before tube insertion and after tube removal to minimize tissue inflammation and scarring. When the plasma coated stent of the invention is used, the use of corticosteroids may be reduced.

In addition, plasma coated stents of the invention reduce the possibility of canalicular narrowing.

Because the plasma deposited coating makes the silicone tube more rigid, it is more difficult to pull the tube through the relatively small diameter canaliculi. When the tube is inserted in the lacrimal system, it is pulled by the surgeon. This stretches the tube and effectively reduces its diameter. Because a tube upon which the plasma coating has been deposited is more rigid, its diameter cannot be reduced sufficiently by stretching. As a result, an attempt to pull it into place will cause the small diameter end of the tube to snap off. To solve this problem, the plasma deposited coating is applied only to the portion of the silicone tube which will remain in the lacrimal system as a stent. The structure of the silicone tube is also modified to have a relatively short "thin" central segment of relatively small outer diameter, a pair of "fat" segments of relatively large outer diameter at opposite ends of the central segment and a pair of "thin" end segments of relatively small outer diameter at the distal ends of the respective fat segments. The thin end segments facilitate threading the silicone tube through the lacrimal system.

The treated stent portion, which comprises all of the central segment and the proximate ends of the fat segments, is the only part of the silicone tube treated with the plasma deposited silicone polymer coating. When the silicone tube is inserted in the lacrimal system, the thin end segments are grasped in the nose and used to pull the untreated fat segment portions into place. As the surgeon pulls the thin end segments down the nose, he also pulls less forcefully in the opposite direction on the fat segments. This stretches and reduces the diameter of the untreated portions of the fat segments and allows them to be pulled through the small diameter canaliculi and then the lacrimal sac and ostium into the nose. If the fat segments had not been stretched with their diameters reduced, the thin end segments would have snapped off as the fat segments entered the canaliculi. The untreated fat segment portions are then grasped in the nose, and the more rigid treated fat segment portions are pulled through the canaliculi, lacrimal sac, and ostium extending into the nose. The fat segments are sufficiently strong, that they will not snap off when so pulled.

In the method of inserting the silicone stent, the end segments are threaded through a respective punctum and canaliculus, through the lacrimal sac, and the ostium into the nasal cavity. First the thin end segments and then the fat segments within the nasal cavity are grasped and pulled down the nasal cavity and out the nostril to position the treated stent portion in the puncta and canaliculi, lacrimal sac, and ostium, extending into the nose. After the tube is in place, most of it is cut off in the nose. The stent portion of the tube, which remains in the lacrimal system, is entirely treated and coated with the plasma deposited silicone polymer coating. The lacrimal mucosa will contact only a treated surface of the tube.

When the tube according to the invention is removed six months after surgery, a dramatic difference can be observed in the ostium when compared to the use of standard, untreated silicone tubing. A larger diameter ostium is achieved, and the patency rate is increased.

BRIEF DESCRIPTION OF THE DRAWINGS

A clearer understanding of the invention will be apparent from the following description and drawings wherein.

DETAILED DESCRIPTION

Figure 1:
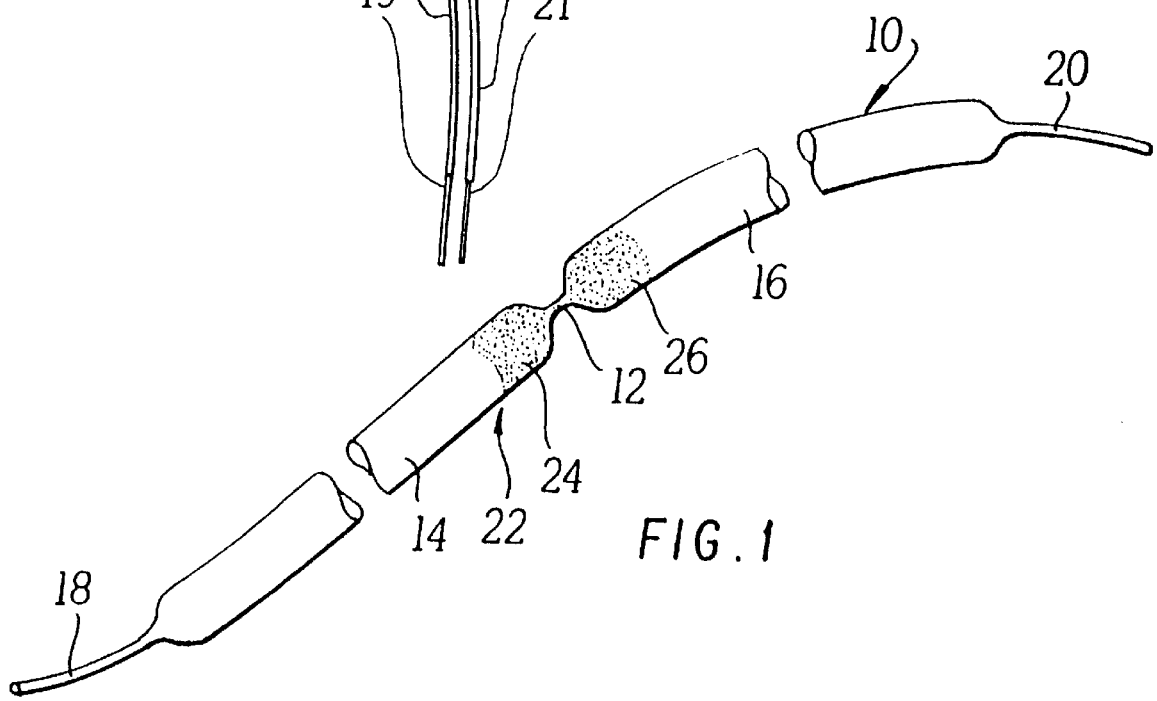
FIG. 1 is a view of a silicone tube according to the invention.

As seen in FIG. 1, which is not drawn to scale, a silicone tube 10 of the invention has a central thin segment 12 of relatively small outer diameter (0.034 inch), a pair of fat segments 14 and 16 of relatively large outer diameter (0.050–0.052 inch) at opposite ends of central segment 12 and a pair of thin end segments 18 and 20 of relatively small outer diameter (0.034 inch) at the distal ends of fat segments 14 and 16. Central segment 12 is 13 mm. long; fat segments 14 and 16 are 15 cm. long; and end segments 18 and 20 are 7 cm. in length. The inner diameter of all segments is 0.016 inch. The transitions between segments are smoothly tapered.

A stent portion 22 comprises all of central segment 12 and the proximate end portions 24 and 26 of fat segments 14 and 16. Stent portion 22, which is 10 cm. in length, is the only part of silicone tube 10 which has been treated to reduce the friction between the tube and lacrimal tissue. The treatment, which provides a smooth, pit-free outer surface to stent portion 22 involves plasma deposition of vaporized silicone based monomer onto the outer silicone surface of stent portion 22. As the silicone monomer is deposited it is covalently bonded to the silicone surface of silicone tube 10 forming a silicone polymer coating which is very smooth and pit-free. Stent portion 22 will have very low friction when it moves relative to lacrimal tissue, as when a patient blinks.

The process for plasma polymerizing a coating onto the surface of the silicone tube 10 is the process shown in U.S. Pat. Nos. 4,824,444 and 4,806,246, which are incorporated therein by reference. Briefly, this process involves moving the silicone tube 10, suitably masked to expose only stent portion 22, through an energy-intensive glow zone in a region between external electrodes of an R.F. capacitively coupled tubular reactor. A silicone based monomer is vaporized and fed into the tubular reactor. The result is the deposition of a silicone plasma polymerizate coating on the surface of stent portion 22.

Figure 3:
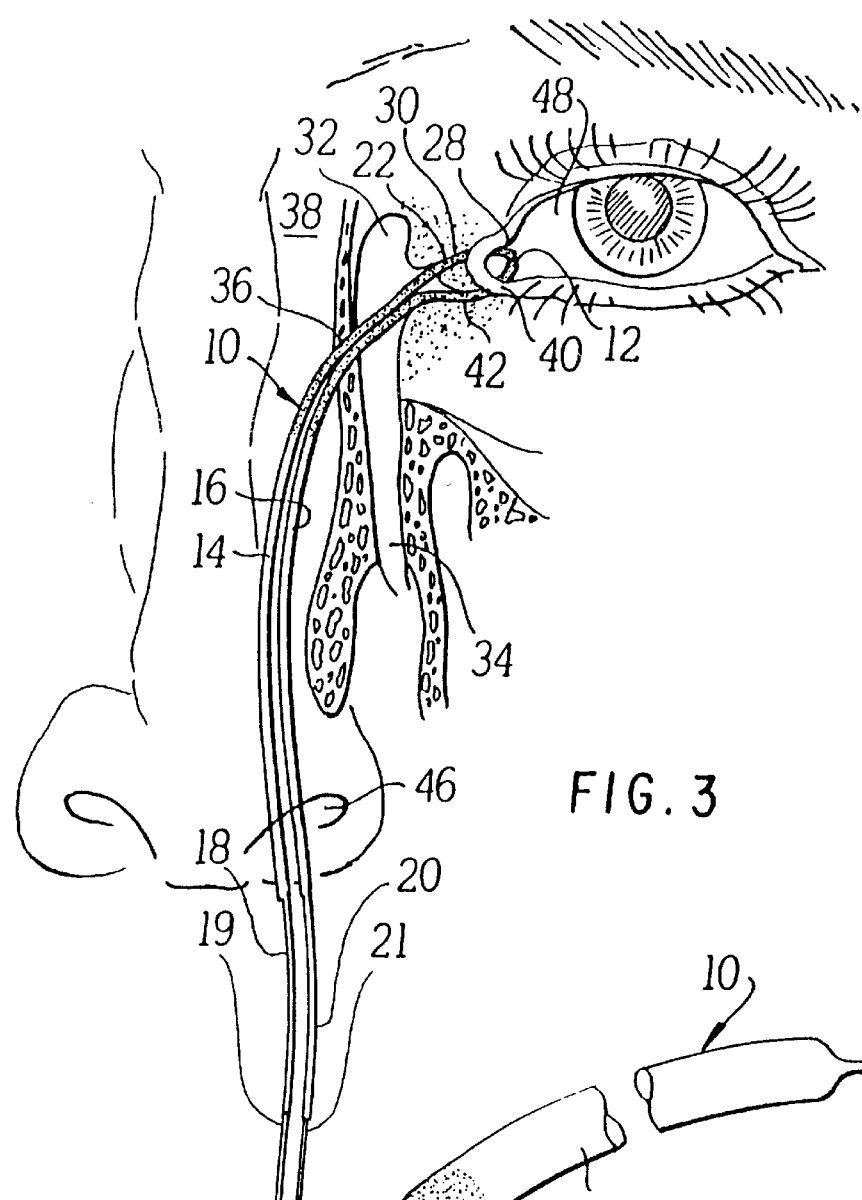
FIGS. 2–4 are views illustrating the method of inserting a silicone tube of the invention.
Figure 2:
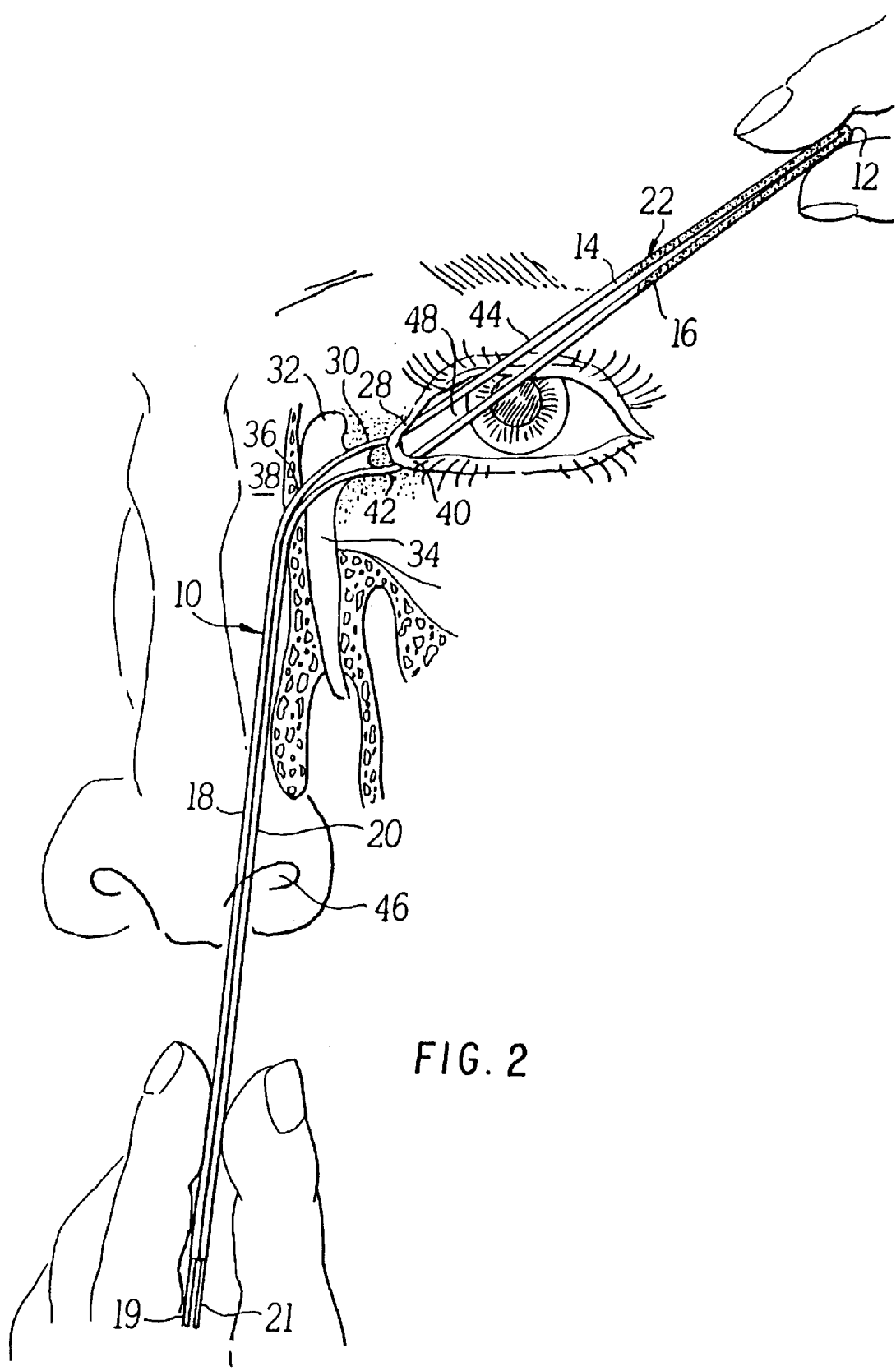
Figure 4:
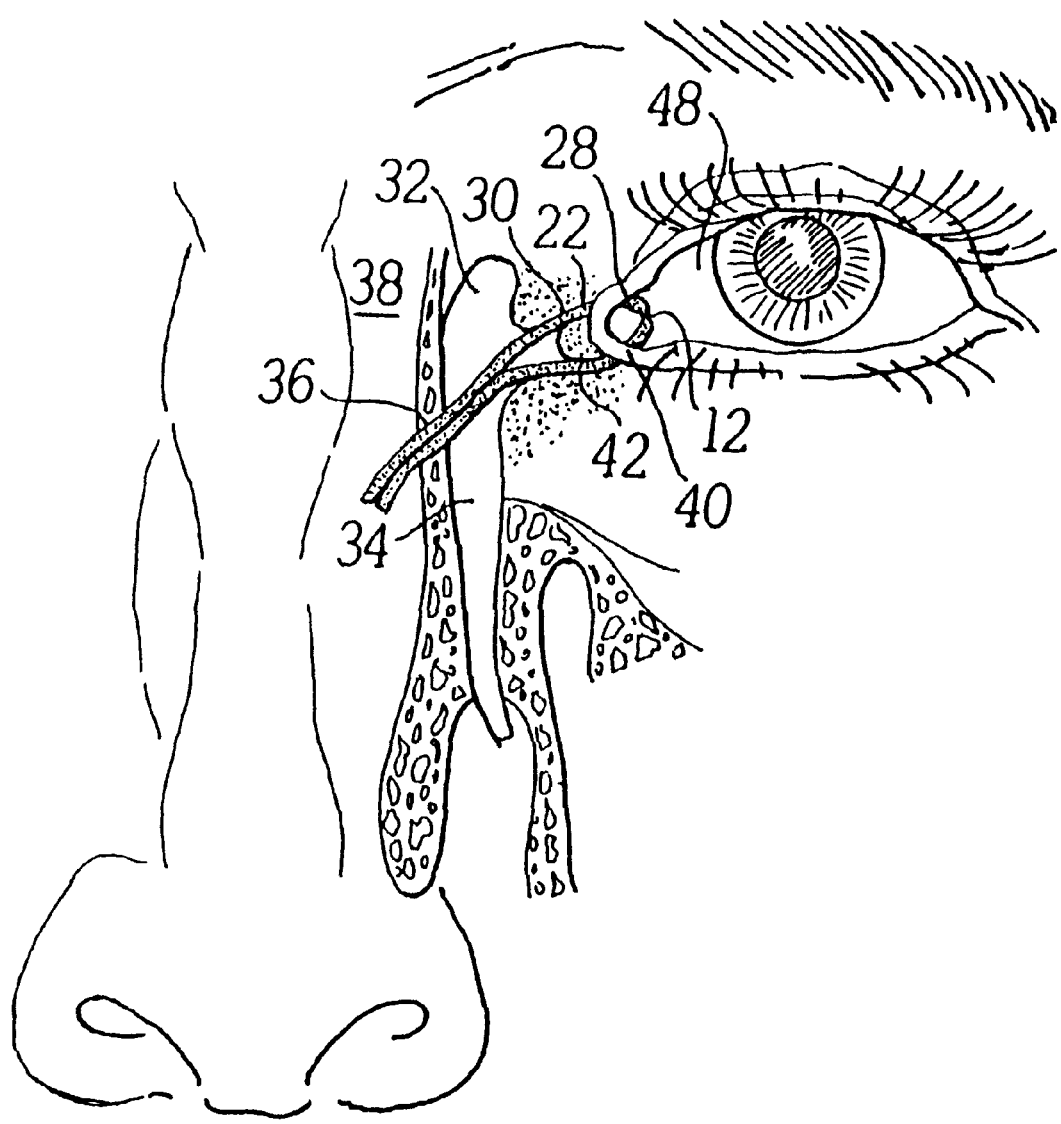

The method of inserting stent portion 22 is illustrated in FIGS. 2–4, which are not drawn to scale. In FIG. 2, silicone tube 10 is shown partially threaded through the lacrimal system. End segment 18, the relatively small outer diameter of which has eased the threading of tube 10, with an attached rigid probe 19 has been threaded from eye 48 through punctum 28, upper canaliculus 30, lacrimal sac 32 (above nasolacrimal duct 34), and ostium 36 (opened by balloon DCR) into the nasal cavity 38. The other end segment 20 with another attached rigid probe 21 is threaded from eye 48 through punctum 40, lower canaliculus 42, lacrimal sac 32 and ostium 36 into the nasal cavity. This leaves a loop 44 with an apex including stent portion 22 and central segment 12. The surgeon applies pulling force at the left (nasal cavity) end of thin end segments 18 and 20 and a smaller pulling force at the apex 44 of silicone tube 10 to apply sufficient tension to tube 10 that fat segments 14 and 16 are stretched and made thinner to more easily be pulled through the puncta, canaliculi and ostium.

As seen in FIG. 3, silicone tube has been fully inserted in the lacrimal system. End segments 18 and 20 with attached probes 19 and 21 extend out the nostril 46. Stent portion 22 is in stenting position, extending from the nasal cavity, ostium 36, through lacrimal sac 32, through lower canaliculus 42, through punctum 40 with central segment 12 looping over the eye 48, back through punctum 28, upper canaliculus 30, lacrimal sac 32, and ostium 36 into the nasal cavity 38. It will be observed that only stent portion 22 is now in the lacrimal system.

With treated stent portion 22 in place in the lacrimal system, the free ends of silicone tube 10 are cut off in nasal cavity 38 at the point on fat segments 14 and 16 where stent portion 22 begins and ends. When the cut-off ends are removed, as shown in FIG. 4, only treated stent portion 22 remains in the lacrimal system where it acts as a stent for the ostium, the canaliculi and the puncta. Because stent portion 22 has been treated to reduce friction between it and the lacrimal tissue, tissue reaction, inflammation and scarring are greatly reduced. Stent portion 22 does not seal ostium 36, canaliculi 30 and 42, and puncta 28 and 40, but allows the flow of tears from the eye through puncta 28 and 40 and ostium 36 into nasal cavity 38. This is particularly the case when a blink causes fluid pressure forcing the tears to flow along the outside of stent portion 22.

After stent portion 22 is left in place for six months, it is removed. There is a dramatic improvement in the condition of the ostium when compared with its condition after six months of use with a standard silicone tube which has not been treated according to the invention to reduce friction. The ostium has a larger diameter; there is less scarring and inflammation and the patency rate is increased.

It should be understood that the foregoing description of the invention is intended merely to be illustrative and other modifications, embodiments and equivalents may be apparent to those skilled in the art without departing from the spirit and scope of the invention.

The invention claimed is a follows:

1. A lacrimal stent apparatus adapted to be inserted in an ostium formed between a patient's lacrimal sac and nasal cavity, said stent apparatus comprising:

an elongated silicone member comprising a central segment having an outer diameter, a pair of non-inflatable middle segments at opposite ends of said central segment, each said middle segment having an outer diameter which is greater than said outer diameter of said central segment, and a pair of end segments at distal ends of the respective middle segments, each said end segment having an outer diameter which is lesser than said outer diameter of said middle segments and having a length which is greater than the length of said central segment, said central segment and the proximate ends of said middle segments forming a stent portion.

2. The lacrimal stent apparatus as defined in claim 1, further including a tapered surface between each of said segments and said middle segments.

3. The lacrimal stent apparatus as defined in claim 1, wherein said silicone member is a tube.

4. A lacrimal stent apparatus adapted to be inserted in an ostium formed between a patient's lacrimal sac and nasal cavity, said stent apparatus comprising:

an elongated silicone member comprising a central segment having an outer diameter, a pair of middle segments at opposite ends of said central segment, each said middle segment having an outer diameter which is greater than said outer diameter of said central segment, and a pair of end segments at distal ends of the respective middle segments, each said end segment having an outer diameter which is lesser than said outer diameter of said middle segments and having a length which is greater than the length of said central segment, said central segment and the proximate ends of said middle segments forming a stent portion, said stent portion being of such length that said stent portion is adapted to extend from said nasal cavity through said ostium, said lacrimal sac, one of the patient's canaliculi, and through one of the patient's puncta, form a loop over the eye, and extend through the other of the patient's puncta, the patient's other canaliculus, said lacrimal sac, and said ostium into said nasal cavity, with said central segment positioned in said loop.

5. A lacrimal stent apparatus as defined in claim 4, wherein said stent portion having a surface which is treated to reduce friction between said stent portion and tissue when said stent portion moves during blinking, whereby lacrimal tissue inflammation and scarring is minimized.

6. The lacrimal stent apparatus as defined in claim 5, wherein said stent portion is treated with a plasma surface treatment.

7. The lacrimal stent apparatus as defined in claim 6, wherein said plasma surface treatment leaves a pit-free polymerized smooth surface.

8. The lacrimal stent apparatus as defined in claim 6, wherein said plasma surface treatment comprises vapor deposition of silicone based monomer which covalently bonds to said stent portion to form a pit-free polymerized smooth surface.

9. The lacrimal stent apparatus as defined in claim 4, further including a tapered surface between each of said end segments and said middle segments.

10. The lacrimal stent apparatus as defined in claim 4, wherein said silicone member is a tube.

11. A lacrimal stent apparatus adapted to be inserted in an ostium formed between a patient's lacrimal sac and nasal cavity, said stent apparatus comprising:

an elongated silicone member comprising a central segment having an outer diameter, a pair of middle segments at opposite ends of said central segment, each said middle segment having an outer diameter which is greater than said outer diameter of said central segment, and a pair of end segments at distal ends of the respective middle segments, each said end segment having an outer diameter which is lesser than said outer diameter of said middle segments and having a length which is greater than the length of said central segment, said central segment and the proximate ends of said middle segments forming a stent portion, said stent portion having a surface which is treated to reduce friction between said stent portion and tissue when said stent portion moves during blinking, whereby lacrimal tissue inflammation and scarring is minimized.

12. The lacrimal stent apparatus as defined in claim 2, wherein said stent portion is treated with a plasma surface treatment.

13. The lacrimal stent apparatus as defined in claim 3, wherein said plasma surface treatment leaves a pit-free polymerized smooth surface.

14. The lacrimal stent apparatus as defined in claim 3, wherein said plasma surface treatment comprises vapor deposition of silicone based monomer which covalently bonds to said portion to form a pit-free polymerized smooth surface.

15. A method of inserting a silicone stent in an ostium between a patient's lacrimal sac and nasal cavity, comprising the steps of:

providing an elongated silicone member having a central segment having an outer diameter, a pair of middle segments at opposite ends of said central segment, each said middle segment having an outer diameter which is greater than said outer diameter of said central segment, and a pair of end segments at distal ends of the respective middle segments, each said end segment having an outer diameter which is lesser than said outer diameter of said middle segments and having a length which is greater than the length of said central segment, said central segment and the proximate ends of said middle segments forming said silicone stent;

threading an end of said silicone member through a punctum and canaliculus from the patient's eye, into and through said lacrimal sac and the ostium, and into the nasal cavity;

grasping said silicone member within the nasal cavity;

pulling said silicone member down the nasal cavity and out a nostril to position said silicone stent in the punctum, canaliculus, lacrimal sac and ostium; and cutting off the remaining portions of said silicone member to leave only said silicone stent in the punctum, canaliculus, lacrimal sac, and the ostium, extending into the nasal cavity.

16. The method as defined in claim 8, wherein said stent has a surface which is treated to reduce friction between said stent and tissue when said stent moves during blinking.

17. The method as defined in claim 8, wherein said threading step further includes threading the other end of said silicone member through a second punctum and canaliculus from the patient's eye, into and through the lacrimal sac and the ostium, and into the nasal cavity; and wherein said cutting off step comprises cutting off both ends of said silicone member after said ends emerge from the ostium into the nasal cavity to leave said stent therein.

18. The method as defined in claim 10, wherein said pulling step comprises pulling both said end segments down the nasal cavity by grasping said end segments while pulling less forcefully on said middle segments in the opposite direction to stretch and effectively reduce the diameter of said middle segments allowing said silicone member to be pulled into position and then grasping said middle segments in the nasal cavity and pulling said stent into position extending from nasal cavity through the ostium, the lacrimal sac, one of the canaliculi, one of the puncta, the other of the puncta, the other of the canaliculi, the lacrimal sac, and the ostium back to the nasal cavity.

19. The method as defined in claim 8, wherein said silicone member is a tube.

* * * * *

UNITED STATES PATENT AND TRADEMARK OFFICE
CERTIFICATE OF CORRECTION

PATENT NO. : 6,113,567
DATED : September 5, 2000
INVENTOR(S) : Bruce B. Becker

It is certified that error appears in the above-identified patent and that said Letters Patent is hereby corrected as shown below:

Title page,
Item [56] under References Cited, insert the following:

U.S. PATENT DOCUMENTS

| DOCUMENT NUMBER | DATE | NAME |
| --- | --- | --- |
| 5,437,625 | 08/01/95 | Kurihashi |
| 5,318,513 | 06/07/94 | Leib et al. |
| 5,169,386 | 12/08/92 | Becker et al. |
| 5,100,689 | 3/31/92 | Goldberg et al. |
| 5,080,924 | 01/14/92 | Kamel et al. |
| 4,824,444 | 4/25/89 | Nomura |
| 4,806,246 | 02/21/89 | Nomura |
| 4,711,820 | 12/08/87 | Ackles et al. |
| 4,380,239 | 04/19/83 | Crawford et al. |
| 4,305,395 | 12/15/81 | Martinez |

Item [56] under References Cited, insert the following:

FOREIGN PATENT DOCUMENTS

| DOCUMENT NUMBER | DATE | COUNTRY |
| --- | --- | --- |
| 9,411,118 | 05/26/94 | WO |

Item [56] under References Cited, insert the following:
-- OTHER DOCUMENTS

1. Kurihashi, Katsuaki, "*Bicanalicular Silicone Intubation: Using Three-Piece Silicone Tubing: Direct Silicone Intubation*", Ophthalmologica, 1993, Vol. 206, pp. 57-68.
2. Allen, et al, "*Dacryocystorhinostomy Failure: Association With Nasolacrimal Silicone Intubation*", Ophthalmic Surgery, July 1989, Vol. 20, No. 7, pp. 486-489.
3. Bartley, George B, "*Acquired Lacrimal Drainage Obstruction: An Etiologic Classification System, Case Reports, and a Review of the Literature. Part 2*", Ophthalmic Plastic and Reconstructive Surgery, 1992, Vol. 8, No. 4, pp. 243-249.
4. Becker, Bruce B, "*Tricompartment Model of the Lacrimal Pump Mechanism*", Ophthamology, July 1992, Vol. 99, No. 7, pp. 1139-1145.
5. Becker, Bruce B. "*Nasal Endoscopy in Dye Testing After Dacryocystorhinostomy*", Ophthalmic Plastic and Reconstructive Surgery, 1990, Vol. 6, No. 1, pp. 64-67. --.

UNITED STATES PATENT AND TRADEMARK OFFICE
CERTIFICATE OF CORRECTION

PATENT NO. : 6,133,567
DATED : September 5, 2000
INVENTOR(S) : Bruce B. Becker

It is certified that error appears in the above-identified patent and that said Letters Patent is hereby corrected as shown below:

<u>Column 7,</u>
Lines 17 and 20, "in claim 8," should be -- in claim 15, --

<u>Column 8,</u>
Line 19, "in claim 8," should be -- in claim 15, --

Signed and Sealed this

Twenty-third Day of October, 2001

Attest:

*Attesting Officer*

NICHOLAS P. GODICI
*Acting Director of the United States Patent and Trademark Office*